(12) United States Patent
Burriesci et al.

(10) Patent No.: US 9,597,211 B2
(45) Date of Patent: Mar. 21, 2017

(54) PROSTHESIS DELIVERY SYSTEM

(75) Inventors: Gaetano Burriesci, London (GB); Spyridon Tzamtzis, London (GB); Alexander Seifalian, London (GB)

(73) Assignee: UCL Business PLC, London (GB)

( * ) Notice: Subject to any disclaimer, the term of this patent is extended or adjusted under 35 U.S.C. 154(b) by 333 days.

(21) Appl. No.: 13/880,341

(22) PCT Filed: Oct. 19, 2011

(86) PCT No.: PCT/GB2011/001504
§ 371 (c)(1),
(2), (4) Date: May 17, 2013

(87) PCT Pub. No.: WO2012/052718
PCT Pub. Date: Apr. 26, 2012

(65) Prior Publication Data
US 2013/0296999 A1      Nov. 7, 2013

(30) Foreign Application Priority Data
Oct. 22, 2010   (GB) .................................. 1017921.6

(51) Int. Cl.
*A61F 2/06*      (2013.01)
*A61F 2/95*      (2013.01)
(Continued)

(52) U.S. Cl.
CPC .............. *A61F 2/95* (2013.01); *A61F 2/2436* (2013.01); *A61F 2/2439* (2013.01); *A61F 2/966* (2013.01); *A61F 2002/011* (2013.01); *A61F 2002/9505* (2013.01); *A61F 2002/9511* (2013.01); *A61F 2002/9522* (2013.01); *A61F 2002/9528* (2013.01); *A61F 2002/9534* (2013.01)

(58) Field of Classification Search
CPC .. A61F 2/95; A61F 2/962; A61F 2/966; A61F 2002/9528; A61F 2002/9534; A61F 2/2436; A61F 2/2439; A61F 2002/011
See application file for complete search history.

(56) References Cited

U.S. PATENT DOCUMENTS 5,749,921 A  *  5/1998  Lenker ...................... A61F 2/95
                                                          606/194
7,329,279 B2     2/2008  Haug et al.
(Continued)

FOREIGN PATENT DOCUMENTS

WO    WO2009/094189    7/2009
WO    WO2010/042950    4/2010
(Continued)

OTHER PUBLICATIONS

Dictionary.com definition for "around" as accessed Aug. 10, 2016; http://www.dictionary.com/browse/around.*
(Continued)

*Primary Examiner* — Jonathan Miles
(74) *Attorney, Agent, or Firm* — Bell & Manning, LLC (57) ABSTRACT

A prosthesis delivery system comprises a sheath defining an axial direction; at least one tether movable axially relative to the sheath; and a holder movable axially within the sheath, configured to constrain radially the tether(s). Collapsing the prosthesis to a collapsed state in the sheath involves constraining radially with a holder the tether(s), attached to the prosthesis; and moving the tether(s) and the holder axially within the sheath such that the prosthesis is forced to collapse into the sheath and the holder is retracted into the sheath.

19 Claims, 4 Drawing Sheets

(51) Int. Cl.
*A61F 2/966* (2013.01)
*A61F 2/24* (2006.01)
*A61F 2/01* (2006.01)

(56) References Cited

U.S. PATENT DOCUMENTS

| | | |
|---|---|---|
| 7,824,443 B2 | 11/2010 | Salahieh et al. |
| 2002/0161377 A1* | 10/2002 | Rabkin ................... A61F 2/95 606/108 |
| 2004/0138734 A1 | 7/2004 | Chobotov et al. |
| 2005/0137686 A1* | 6/2005 | Salahieh et al. ............ 623/2.11 |
| 2006/0173524 A1 | 8/2006 | Salahieh et al. |
| 2009/0192585 A1 | 7/2009 | Bloom et al. |
| 2009/0270966 A1 | 10/2009 | Douk et al. |
| 2010/0049313 A1 | 2/2010 | Alon et al. |

FOREIGN PATENT DOCUMENTS

| | | |
|---|---|---|
| WO | WO2010/079427 | 7/2010 |
| WO | WO2010/112844 | 10/2010 |

OTHER PUBLICATIONS

Search Report issued in GB Application No. 1017921.6, Dec. 21, 2010.
International Search Report and Written Opinion issued in PCT/GB2011/001504, Dec. 23, 2011.

\* cited by examiner

PROSTHESIS DELIVERY SYSTEM

This application is a National Stage of International Application No. PCT/GB2011/001504, filed Oct. 19, 2011, which claims the benefit of GB Patent Application No. 1017921.6, filed Oct. 22, 2010, the contents of which are herein incorporated by reference.

The present invention relates to a prosthesis delivery system, a method for collapsing a prosthesis into a sheath and a method for delivering a prosthesis to a target position. More particularly, but not exclusively, the present invention relates to a method for delivery and recapture of a heart valve.

In the following a prosthetic collapsible heart valve will be used as an example of a percutaneously implantable prosthesis that needs to be delivered to an organ, in this case the heart. For brevity, the prosthetic heart valve will generally simply be referred to as a "heart valve".

In recent years percutaneous implantation of heart valves has emerged as a valid alternative to surgical valve replacement. In this context, percutaneous refers to accessing the heart with a minimally invasive technique, as opposed to full open-heart surgery. Percutaneous techniques include endovascular implantation and thorasic-microsurgery. According to these techniques, access is done via needle-puncture of the skin, and does not require scalpel incisions to open the thorasic cavity and expose the heart. Another technique, known as surgical transapical access, to access the heart involves puncturing the apex of the ventricle so as to access the heart with minimal access surgery.

For percutaneous delivery of a heart valve, the valve must be collapsible to a compressed state such that it can be delivered e.g. through the venous or arterial system using a catheter and a guidewire, to the required position, and then expanded in situ into its normal operating state. In many cases known in the art, the support structure is essentially similar to a stent used for angioplasty.

PCT/GB 10/000627, which is herein incorporated by reference in its entirety, discloses a heart valve prosthesis comprising a support structure and a flow-control structure. The support structure comprises a framework deformable between an expanded state and a compressed state and vice versa. The support structure supports the flow-control structure. The flow-control structure is for permitting blood flow in an axial direction of the prosthesis, and for restricting blood flow in a direction opposite to the axial direction. At least one end of the support structure comprises a plurality of apexes of the framework of the support structure. The support structure is collapsible into the compressed state by pulling on the apexes, to enable it to be drawn into a sheath in the compressed state. The sheath has an inner radial dimension smaller than the radial dimension of the support structure in the expanded state.

This heart valve can be implanted by retrograde access or antegrade access. In both cases, the heart valve is collapsed to a compressed state and held within the sheath on the end of a guidewire that is inserted into the vascular system through a catheter. The heart valve can be inserted by surgical transapical access.

Figure 10:
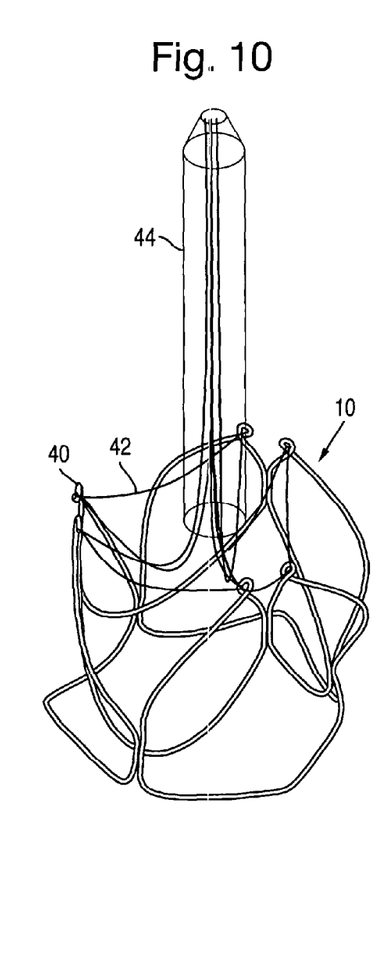
FIGS. 10 to 13 show the sequence of retrieving a heart valve back into the sheath as known in the prior art.
Figure 11:
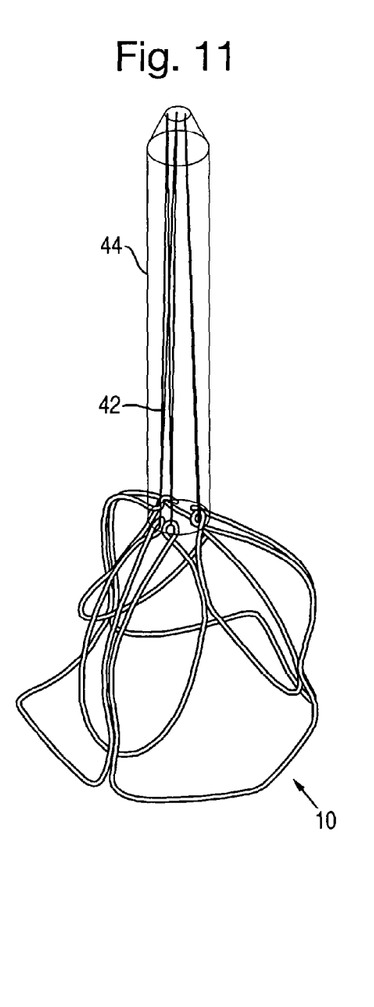
Figure 12:
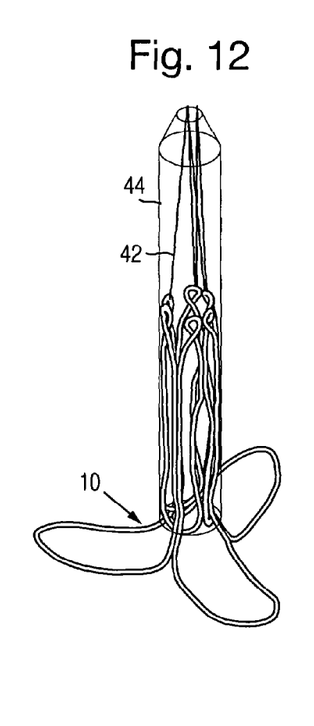
Figure 13:
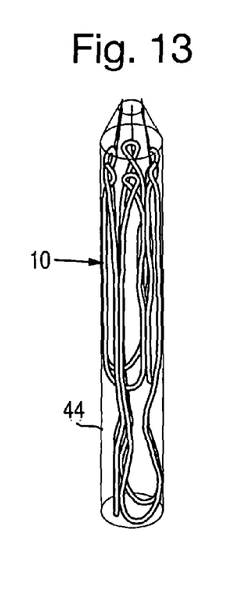

FIGS. 10 to 13 show a sequence of snapshots of collapsing the prosthetic heart valve into a compressed state. In FIG. 10, loops of filiform material 42 pass through pairs of adjacent loops 40 of the support structure of the prosthesis 10. The threads of filiform material 42 pass out through the sheath 44. When the filiform material is pulled, the loops 40 are gathered together as shown in FIG. 11, and then the upper petal-like shapes of the prosthesis 10 collapse and can be withdrawn into the sheath 44 as shown in FIG. 12. In this state, the lower petal-like shapes have also become folded. On further pulling of the filiform material, the structure is completely withdrawn into the sheath 44 as shown in FIG. 13.

When the sheath 44 has been delivered, for example endovascularly on the end of a guidewire to the required implantation position, the reverse sequence of FIGS. 10 to 13 is performed and the sheath 44 is withdrawn away from the heart valve structure. The lower petal-like protrusions expand first as shown in FIG. 12 and enable the heart valve to be initially correctly positioned, including rotational positioning. Further withdrawal of the sheath 44 allows the heart valve to self-expand as shown in FIGS. 11 and 10. In the event that the heart valve needs to be repositioned or retrieved entirely, the filiform material 42 can be pulled again to collapse the structure into its compressed state, either partially or fully. When the positioning is finalised, the filiform material 42 and the sheath 44 can be completely withdrawn via the reverse route through which access was obtained.

However, there are a number of problems with known systems for percutaneous delivery of prosthetic heart valves. One problem is achieving the compressed state of the heart valve in the sheath, the heart valve being both radially and axially compact to fit within the sheath so as to pass round tortuous bends in the vascular system when being delivered to the heart. In particular, it can be difficult to collapse the heart valve sufficiently such that it can be fully inserted into the sheath. Another problem is that the heart valve can catch on the rim of the sheath and jam when it comes into contact with the sheath, thereby preventing the heart valve from being fully inserted. A further problem is that while inserting the heart valve into the sheath, the heart valve may get damaged or destroyed.

The present invention seeks to alleviate, at least partially, some or any of the above problems.

According to an aspect of the present invention, there is provided a prosthesis delivery system comprising a sheath, at least one tether and a holder. The sheath defines an axial direction. The at least one tether is movable axially relative to the sheath. The holder is movable within the sheath, and is configured to constrain radially the at least one tether.

According to a further aspect of the present invention, there is provided a method of collapsing a prosthesis to a collapsed state in a sheath. The method comprises the steps of:

constraining radially with a holder at least one tether, attached to the prosthesis; and moving the at least one tether and the holder axially within the sheath such that the prosthesis is forced to collapse into the sheath and the holder is retracted into the sheath.

According to a further aspect of the present invention, there is provided a method of delivering a prosthesis collapsed in a sheath to a target position. The method comprises the steps of:

retracting the sheath axially away from the prosthesis attached to at least one tether such that the prosthesis partially expands from the collapsed state, wherein the at least one tether to which the prosthesis is attached is constrained radially by a holder that is movable axially within the sheath;

positioning in the target position the prosthesis that is in a partially collapsed state, attached to the at least one tether; and detaching the at least one tether from the prosthesis.

Embodiments of the invention will now be described, by way of example only, with reference to the accompanying drawings in which.

Figure 1:
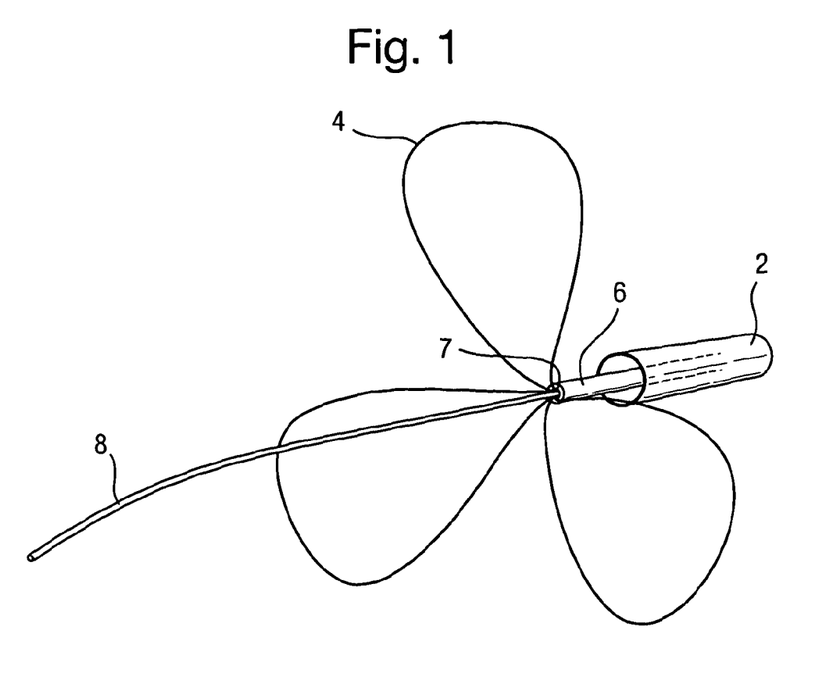
FIG. 1 shows a prosthesis delivery system of an embodiment of the present invention.

FIG. 1 depicts a schematic perspective view of an embodiment of the prosthesis delivery system. The apparatus comprises a sheath 2, at least one tether 4 and a holder 6. Preferably, the apparatus is connected to a guidewire 8.

In particular, FIG. 1 depicts an embodiment of the apparatus, comprising an internal tube (i.e. holder 6), hosting one or more control thread loops (i.e. tethers 4), a guidewire 8 for endovascular guidance, and an external sheath 2 to collapse fully the prosthesis 10 and contain it in the collapsed configuration.

In an embodiment, the delivery system of the present invention comprises a holder 6 (which may take the form of a tube) within a sheath 2 (which may take the form of a tube). The tethers 4 (which may comprise wires) are fed through the holder 6 and when the tethers 4 are pulled, the top loops of the prosthesis 10 (which may be a valve) draw together. Once in this position the prosthesis 10 can then be pulled into the sheath 2 and removed. The delivery system of the present invention has an advantage over delivery systems that do not have a holder 6 in that the risk of the top loops of the prosthesis 10 catching on the rim of the sheath 2 and jamming is reduced. Such undesirable catching and jamming can happen particularly if the top loops of the prosthesis 10 are not drawn together adequately when the prosthesis 10 is being pulled into the sheath 2.

The invention will be described in further detail below.

The guidewire 8 helps to control the movement of the apparatus through the vasculature of a living being. The apparatus is for delivering a prosthesis to an organ of a living being. The living being may be a mammal and, in particular, may be a human. The apparatus is a size suitable for being inserted into the vasculature of the living being.

The sheath 2 is longitudinal in shape and defines an axial direction. The sheath 2 is for housing the prosthesis 10 when the prosthesis 10 is in a collapsed state. The sheath 2 is configured to move through the vasculature of the living being. The purpose of the sheath 2 is to protect the prosthesis 10 during its delivery from outside the living being to the organ. The prosthesis 10 is collapsed to a compressed state and held within the sheath 2 on the guidewire 8 that is inserted into the vascular system through a catheter (not shown).

The sheath 2 may take the form of a tube open at both ends. Preferably, the sheath 2 is substantially cylindrical, having a substantially constant diameter throughout its axial (i.e. longitudinal) length. The diameter of the sheath 2 is great enough such that the prosthesis 10 fits inside the sheath 2 when it is in the compressed state. However, when the prosthesis 10 is its expanded shape, the prosthesis 10 does not fit inside the sheath 2. The sheath 2 has an inner radial dimension smaller than the radial dimension of the prosthesis 10 in the expanded state.

The diameter of the sheath 2 is small enough such that it can fit inside the vascular system of the living being. The prosthesis 10 is inserted into the sheath 2 and removed from the sheath 2 at one opening of the sheath 2, which may be termed the lead end 3 of the sheath 2.

The at least one tether 4 is movable axially relative to the sheath 2. Preferably, the apparatus comprises a plurality of tethers 4. For example, as depicted in FIG. 1, the apparatus may comprise three tethers 4. The number of tethers 4 that may be used is not particularly limited and may be two, four or more. In the following description, for clarity it will be assumed that there is a plurality of tethers 4.

The tethers 4 are configured to attach to the prosthesis 10. For example, in the case of a prosthetic heart valve, which comprises a support structure and a flow-control structure, the tethers 4 are configured to attach to the framework of the support structure of the prosthesis 10. The tethers 4 may extend along the length of the sheath 2. The tethers 4 are disposed within the sheath 2. Preferably, the tethers 4 are configured to be extendable beyond the lead end 3 of the sheath 2. The tethers 4 are not integrally connected to the sheath 2.

The tethers 4 are configured to attach to the prosthesis 10 at a lead end 5 of the tethers 4. The tethers 4 may be configured to be controllable so as to be detachable from the prosthesis 10, via the end of the tethers 4 that is opposite to the lead end 5 of the tethers 4. The purpose of this is that when the prosthesis is attached to the delivery system via the tethers 4 and is in the correct place in the vascular system ready to be delivered, the prosthesis 10 can be left at the target position and the delivery system retrieved out of the body.

Figure 5:
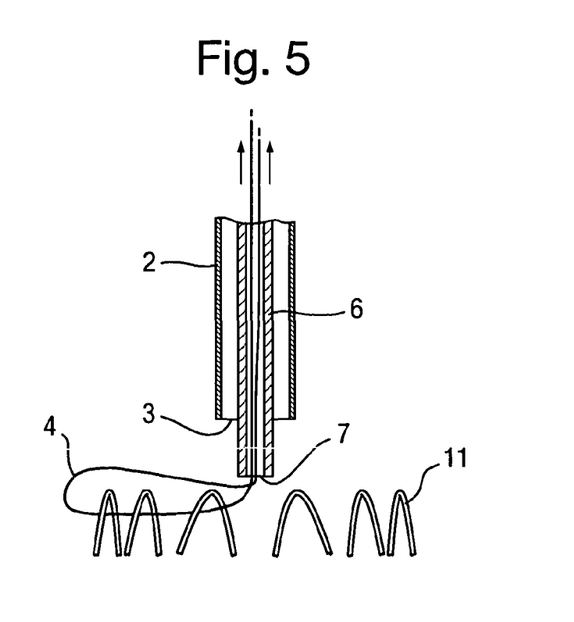
FIG. 5 shows the step of detaching the at least one tether from the prosthesis.

The detachment of the tethers 4 from the prosthesis 10 may be performed either by use of a guidewire attached the tethers 4. Each tether 4 may have its own guidewire, or a plurality of tethers 4 may share a single guidewire. Alternatively, the detachment of the tethers 4 from the prosthesis 10 can be controlled by direct manipulation of the tethers 4 themselves. The tethers 4 can be directly manipulated to detach from the prosthesis 10 in the case that the tethers 4 extend from the lead end 5 to a position outside the body of the living being. FIG. 5 depicts such a construction.

The tethers 4 may comprise an unclosed loop of filiform material. The loop is formed at the lead end 5 of the tethers 4. The two ends of the unclosed loop of filiform material are at the opposite end (i.e. the control end) of the tethers 4. In this case, the detachment of the tethers 4 from the prosthesis 10 can be performed by manipulation at the open ends of the unclosed loop of filiform material.

As will be described in further detail below in relation to FIGS. 6 to 9, the tethers 4 may comprise a hooked rib (i.e. a rib 12 with a hook 13 at its lead end). In this case, the hooked rib may be attached to a guidewire for controlling the detachment of the tether 4 from the prosthesis 10.

The apparatus may comprise a mixture of tethers 4 that comprise unclosed loops of filiform material and tethers 4 that comprise hooked ribs.

The holder 6 is movable axially within the sheath 2. The holder is configured to constrain radially the tethers 4. The purpose of the constraining is to allow one end of the prosthesis 10 to be held by the tethers 4 in a collapsed state such that when the partially collapsed prosthesis 10 is fully inserted into the sheath 2, the part of the prosthesis 10 that first enters the sheath 2 does not catch on the edges of the sheath 2.

The holder 6 may hold the tethers 4 in a convergence region 7. The convergence region 7 may be within an aperture at the lead end 3 of the sheath 2 when viewed in the axial direction. The purpose of the convergence region 7 is to allow one end of the prosthesis 10 to be collapsed in the convergence region 7 such that the collapsed end of the prosthesis 10 fits inside an aperture of the lead end 3 of the sheath 2. For this reason, the convergence region 7 is within the internal region of the sheath 2.

The holder 6 may encircle, or surround the tethers 4 when viewed in cross section. The holder groups, or collects the tethers 4 together. Preferably, the holder 6 forms a closed loop when viewed in cross section.

The radial constraint of the tethers 4 by the holder 6 allows a clearance between the outside of the collapsed end of the prosthesis 10 (which is attached to the tethers 4) and the inner surface of the sheath 2 such that the collapsed end of the prosthesis 10 does not come into contact with the sheath 2. Of course, when the prosthesis 10 is fully inserted into the sheath 2, parts of the prosthesis 10 come into contact with the internal surface of the sheath 2. However, when the insertion process begins, the prosthesis 10 can be partially collapsed such that the end of the prosthesis closest to the sheath 2 is collapsed and attached to the radially constrained tethers 4 such that the collapsed part of the prosthesis 10 does not catch on the sheath 2 as it is inserted. Subsequently, as the sheath 2 is forced around the rest of the prosthesis 10 (e.g. the uncollapsed part of the prosthesis 10), the prosthesis 10 does not become jammed, but is forced to collapse by the pressure of the sheath 2.

The convergence region 7 is a region just beyond the lead end of the holder 6. The lead ends 5 of the tethers 4 constrain the collapsed end of the prosthesis 10 at the convergence region 7. The convergence region 7 may be a convergence area, within the cross sectional area of the sheath 2 when viewed in the axial direction. The sheath 2 may have a cross sectional area consistent throughout its length. However, if the cross sectional area of the sheath 2 varies throughout its length, then the relevant cross sectional area is the cross sectional area of the sheath 2 at the lead end 3 of the sheath 2. The lead end 3 is the end at which the prosthesis 10 enters and exits the sheath 2.

Figure 2:
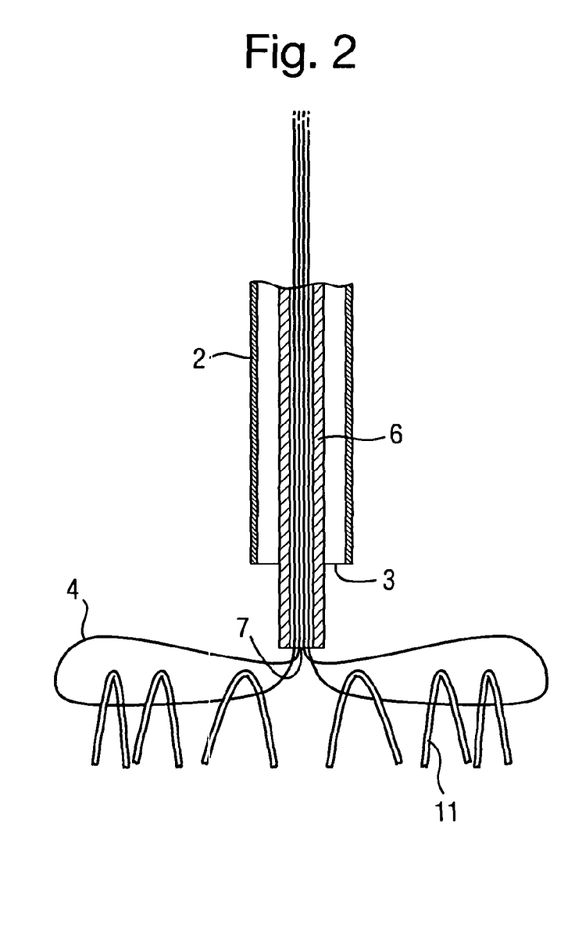
FIGS. 2 to 4 show the sequence of collapsing the prosthesis into the sheath of an embodiment of the delivery system of the present invention.
Figure 3:
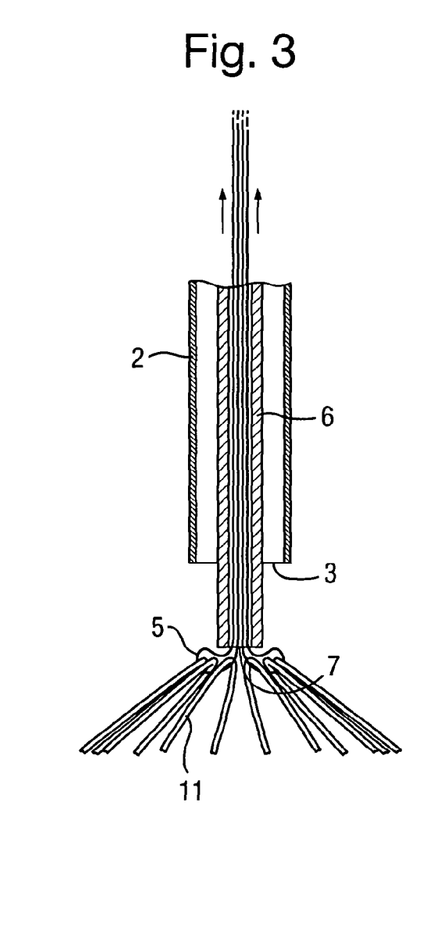
Figure 4:
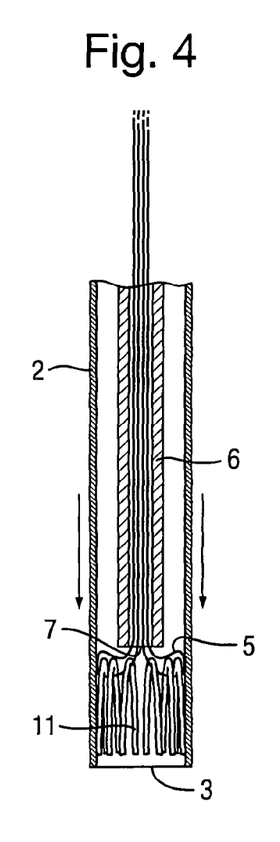

FIGS. 2 to 4 depict a method of collapsing a prosthesis 10 into the sheath 2 of the delivery system. In FIGS. 2 to 4, the tethers 4 comprise unclosed loops of filiform material. However, as mentioned above and depicted in FIGS. 6 to 9, the present invention may also be implemented with tethers 4 comprising hooked ribs 12, 13.

In FIG. 2, the loops of the tethers 4 are attached to the prosthesis 10. The prosthesis may comprise a support structure having a framework with distal cells. The distal cells have apexes 11. The support structure is collapsible from the fully expanded state into the compressed state by pulling on the apexes 11. This enables the support structure to be drawn into the sheath 2 in the compressed state. The sheath 2 has an inner radially dimension smaller than the radial dimension of the support structure in the expanded state.

Each of the tethers 4 forms a loop that passes through a number of the distal cells of the framework of the prosthetic device. The tethers 4 are attached to the apexes 11 of the support structure of the prosthesis 10 at the lead end 5 of the tethers 4. The tethers 4 may be looped around one or more of the apexes 11. In FIG. 2, the two tethers 4 are depicted as being looped around three apexes 11 each.

The method of collapsing involves constraining radially the tethers 4 with the holder 6. The holder 6 fits within the sheath 2. Hence the radial constraint results in a clearance between the constrained section of the tethers 4 and the inner surface of the sheath 2. The tethers 4 are attached to the prosthesis 10. This state is depicted in FIG. 2.

Subsequently, the tethers 4 and the holder 6 are moved axially within the sheath 2 such that the prosthesis 10 is forced to collapse into the sheath 2 and the holder 6 is retracted into the sheath 2. The resulting state is depicted in FIG. 4. The arrows in FIG. 4 indicate the direction of movement of the sheath 2 relative to the holder 6 and the tethers 4.

More particularly, the collapse of the device into the delivery system (depicted in FIGS. 2 to 4) may be achieved by retracting the tethers 4 into and/or through the holder 6, which may be an internal tube, in order to group the distal edges of the prosthesis frame in the convergence region 7. The dimensions of the convergence region 7 are smaller than the diameter of the external sheath 2 (see FIG. 3). Hence, keeping the tethers 4 fixed in this position, the external sheath 2 is advanced relatively to the prosthesis so as to force the prosthesis to collapse into it (see FIG. 4). This operation can be repeated once the prosthesis 10 has been fully deployed into the target position of the anatomical region. This process may be performed so as to achieve the complete retrieval of the prosthesis 10.

Preferably, the method comprises the step of retracting the tethers 4 relative to the holder 6 so as to collapse partially the prosthesis 10 such that the collapsed end of the prosthesis 10 fits within an aperture at the lead end 3 of the sheath 2. For example, according to the embodiment depicted in FIGS. 2 to 4, the step of moving the tethers 4 and the holder 6 axially relative to the sheath 2 is broken up into two stages.

In the first stage, the prosthesis 10 is partially collapsed such that one end of the prosthesis 10 fits within an aperture at the lead end 3 of the sheath 2. In order to perform this first stage, preferably the tethers 4 are movable axially within the holder 6. The tethers 4 are pulled such that they are retracted into/towards the sheath 2. The arrows in FIG. 3 indicate the direction in which the tethers 4 are pulled. The end of the prosthesis 10 closest to the sheath 2 collapses into the convergence region 7 because the tethers 4 are constrained radially by the holder 6.

In the second stage, the tethers 4 together with the holder 6 are retracted into/through the sheath 2. The collapsed end of the prosthesis 10 enters into the lead end 3 of the sheath 2 without touching the edges of the sheath 2. Once the collapsed apexes 11 are retracted into the sheath 2, other parts of the prosthesis 2 come into contact with the sheath 2, thereby having the effect of forcing the rest of the prosthesis 10 to collapse into the sheath 2.

Prior to the state depicted in FIG. 2, the lead ends 5 of the tethers 4 are attached to the prosthesis 10. This step may be performed outside the body of the living being. However, as explained in relation to FIGS. 6 to 9, if a tether 4 comprising a hooked rib 12, 13 is used, this step can be performed in the body of the living being.

As depicted in FIGS. 2 to 4, the holder 6 may comprise a tube that is substantially co-axial with the sheath 2. The holder 6 does not necessarily have to take the form of a tube. In an embodiment, the holder 6 may comprise an annular ring. Preferably, the holder 6 is on a guidewire for endovascular guidance.

The holder 6 is different from the sheath 2. The holder 6 fits inside the sheath 2. When the prosthesis 10 is in the sheath 2 in the collapsed state, the holder 6 may be in the sheath 2. Preferably, the holder is not attached to the sheath 2. There may be a clearance gap between the outer surface of the holder 6 and the inner surface of the sheath 2.

Alternatively, the holder 6 may be attached to the sheath 2 provided that the holder 6 is movable axially relative to the sheath 2.

The holder 6 may be movable relative to the sheath 2 between an extended position (as depicted in FIG. 2) and a retracted position (see FIG. 4). In the extended position, a lead end of the holder 6 extends beyond a lead end 3 of the sheath 2. In the retracted position, the lead end 3 of the sheath 2 extends beyond the lead end of the holder 6.

Preferably, a lead end of the holder 6 is configurable to extend beyond a lead end 3 of the sheath 2. The holder 6 may be initially positioned such that the convergence region 7 into which the collapsed apexes 11 are to be fit is extended beyond the lead end 3 of the sheath 2. This allows the partially collapsed end of the prosthesis 10 to be collected away from the lead end 3 of the sheath 2 (see FIG. 3) before the sheath 2 is forced around the rest of the prosthesis 10. Hence, it is preferable that the lead end of the holder 6 is initially beyond the lead end 3 of the sheath 2 before being moved to be inside the sheath 2 (as shown in FIG. 4).

However, it is possible that the desired function, namely collecting the collapsed end of the partially collapsed prosthesis 10 such that it does not come into contact with the sheath 2 when the process of forcing the prosthesis 10 into the sheath 2 is begun, can be performed by having the lead end of the holder 6 not extending beyond the lead end 3 of the sheath 2.

This is because as depicted in FIG. 3, the collapsed end of the prosthesis 10 forms a tapered shape, with the narrow section closest to the sheath 2. As such, it is possible for the lead end of the holder 6 to be slightly within the sheath 2, while still having the collapsed end of the prosthesis 10 to be initially inserted into the sheath 2 without touching the sheath 2. However, if the lead end of the holder 6 is retracted too far behind the lead end 3 of the sheath 2, then it would not be possible to collapse one end of the prosthesis 10 such that it does not come into contact with the sheath 2.

When the prosthesis 10 is in the collapsed state within the sheath 2 as depicted in FIG. 4, it is ready to be delivered to a target position of an anatomical region, for example in the heart of a living being.

As mentioned above, the sheath 2 with the collapsed prosthesis 10 inside it is entered into the vascular system of the living being via a catheter. The sheath 2 is moved within the vascular system along the guidewire 8.

The method of delivering the prosthesis 10 to the target position involves retracting the sheath 2 axially away from the prosthesis 10 that is attached to the tethers 4. This results in the prosthesis 10 partially expanding from the collapsed state. This step is depicted in the transition from FIG. 4 to FIG. 3.

The tethers 4 to which the prosthesis 10 is attached are constrained radially by the holder 6. As a result, the prosthesis 10 is attached to the tethers 4 in the partially collapsed state.

The delivery of the prosthesis 10 further involves positioning in the target position the prosthesis 10 that is in the partially collapsed state and attached to the tethers 4. The position of the prosthesis 10 can still be controlled because it is still attached to the tethers 4.

Once the prosthesis 10 is in the target position, the tension on the tethers 4 is relaxed, thereby allowing the prosthesis 10 to fully expand (subject to the constraints of the vasculature in which it is situated).

Hence in summary, the deployment of the prosthesis 10 is achieved by retracting the external sheath 2, leaving the prosthesis 10 engaged only on the tethers 4. In this stage, the prosthesis is still firmly fixed to the delivery system, and can be manoeuvred and repositioned. Releasing the tension from the tethers 4, the prosthesis 10 deploys fully. If necessary, the collapse sequence of operations can be repeated to retrieve the prosthesis 10.

The full expansion of the prosthesis 10 is achieved by simply relaxing the tension on the tethers 4. After the release of the expansion of the prosthesis 10, the delivery system can be moved away from the prosthesis 10 following the vascular route, keeping the tethers 4 connected to the prosthesis 10. The valve positioning and haemodynamic performance can be checked with state of the art techniques (e.g. by fluoroscopy, echocardiography and/or aorthography) and, if necessary, the catheter can be readvanced and the prosthesis 10 safely recollapsed and repositioned (or completely removed and exchanged for another solution) by pulling the tethers 4. This feature of allowing the prosthesis 10 to expand fully while still being connected to the tethers 4 means that it is not necessary for the delivery system to retrieve the valve to be kept in proximity of the prosthesis 10. This reduces the possibility of the delivery system from interfering with the performance of the prosthesis 10 when these are verified.

Once the procedure is satisfactorily completed, the tethers 4 can be detached from the prosthesis 10 and extracted.

FIG. 5 depicts the prosthesis delivery system during a process of detaching the tether 4 from the prosthesis 10. In the embodiment depicted in FIG. 5, the tether 4 comprises an unclosed loop of filiform material. The loop can be detached from the prosthesis 10 by pulling on one of the open ends of the loop of filiform material. This unthreads the loop from the prosthesis 10. Hence, when the positioning of the prosthesis 10 in the target position is correct, the tethers 4 may be removed from the apparatus by disengaging one of their terminations and retracting the other.

In FIG. 5, two tethers 4 are depicted at different stages of detachment. The tether 4 shown in the left hand side of FIG. 4 remains looped around apexes 11 of the prosthesis 10. However, the tension has been released and one of its terminations is moving through the sheath 2 so as to pass through the apexes 11, thereby detaching the tether 4 from the prosthesis 10. An arrow is shown indicating the direction of movement of the other end of the tether 4, namely away from the prosthesis 10. The tether 4 shown in the right hand side of FIG. 4 is at a later stage of detachment and is no longer attached to the prosthesis 10. By pulling the tether 4 in the direction of the arrow, the tether 4 is removed completely from the delivery system.

Figure 6:
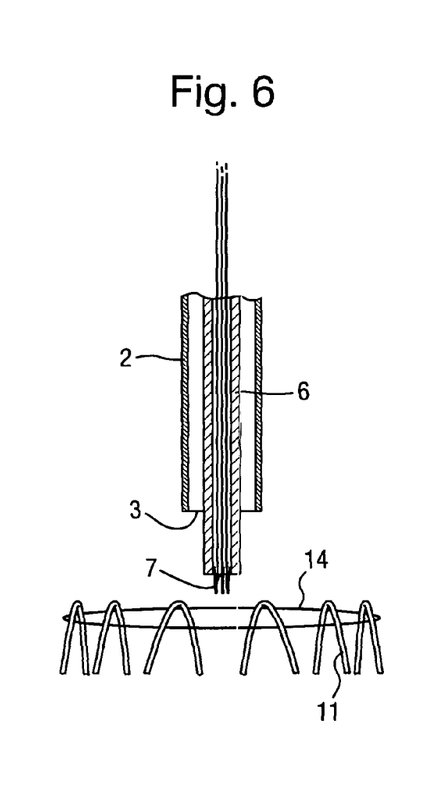
FIGS. 6 to 9 show the sequence of collapsing the prosthesis into the sheath of an embodiment of the delivery system of the present invention.

FIGS. 6 to 9 depicts another embodiment of the present invention in which the tethers 4 comprise a hooked rib, 12, 13 configured to be movable axially relative to the holder 6. The hooked rib 12, 13 is configured to move between a collapsed position and an expanded position. In the collapsed position, which is depicted in FIG. 6, the hooked rib 12, 13 is held by the holder 6 in an elastically deformed state. In the expanded position, the hooked rib 12, 13 extends radially beyond the holder 6.

Figure 7:
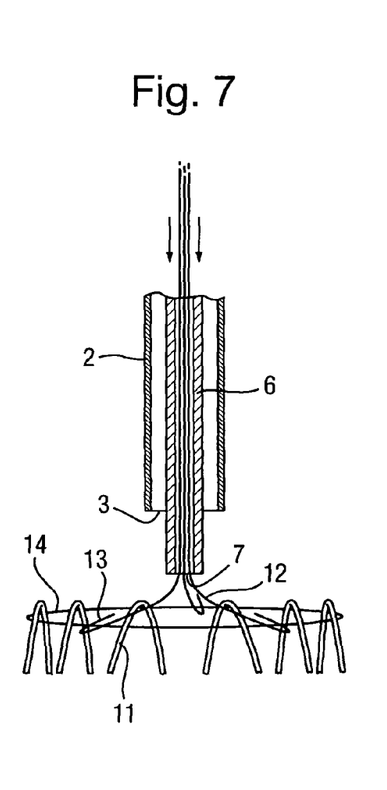

The hooked rib 12, 13 comprises a hook 13 on the end of a rib 12. The hook 13 may be formed integrally with the rib 12. Alternatively, the hook 13 may be a separate member from the rib 12, connected to the rib 12. The hook 13 is designed to attach to the prosthesis 10. As depicted in FIGS. 6 and 7, the prosthesis 10 may comprise a permanent wire 14, which is suitable for the hook 13 to attach to.

The rib 12 is formed of an elastic material. In the collapsed position depicted in FIG. 6, the ribs 12 are constrained by the holder 6. When the hooked ribs 12, 13 are moved from the collapsed state to the expanded position (depicted in FIG. 7) the hooked ribs 12, 13 extend beyond a lead end of the holder 6. The hooked ribs 12, 13 extend through the holder 6. Due to the elastic nature of the ribs 12, the ribs extend radially beyond the holder 6. This allows the ribs to be attached by the hooks 13 to the prosthesis 10 even when the prosthesis 10 is in its fully expanded position.

More particularly, an embodiment of the present invention comprises a holder 6, which may comprise an internal tube, hosting one or more ribs 12 made terminating with hooks 13 (and a guidewire), and an external sheath 2 to collapse fully the prosthesis 10 and contain it in the collapsed configuration. The prosthesis 10 may include a permanent wire passing through all distal cells of the framework of the support structure of the prosthesis.

Once the hooks 13 are attached to the prosthesis 10 in the expanded state, the process for collapsing the prosthesis into the sheath 2 is similar to the process for the embodiments in which the tethers 4 comprise a loop of filiform material as described above. The tethers 4 comprising the hooked ribs 12, 13 are moved axially through the holder 6 so as to bring the lead end of the tethers 4 (i.e. the hooks 13) towards the holder 6 so as to collapse partially the prosthesis 10. This step is seen as a transition from the state depicted in FIG. 7 to the state depicted in FIG. 8. The arrows in FIG. 8 indicate the direction of movement of the tethers 4 relative to the holder 6. Subsequently, the sheath 2 is moved axially relative to the tethers 4 and the holder 6 such that the prosthesis 10 is forced to collapse into the sheath 2 and the holder 6 is retracted into the sheath 2. This results in the state depicted in FIG. 9.

Figure 8:
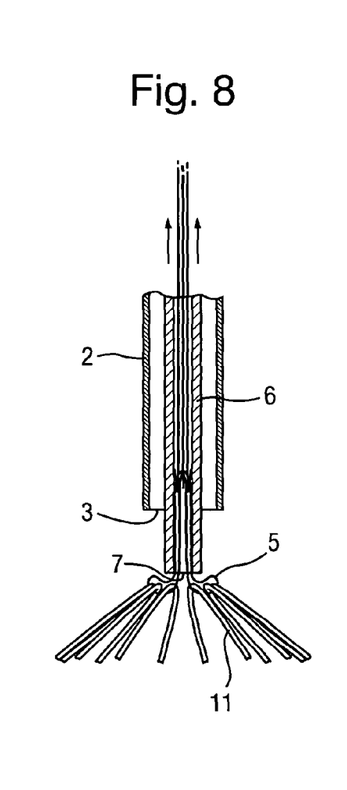
Figure 9:
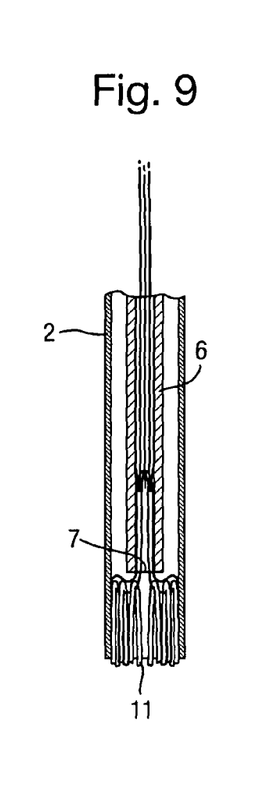

To retrieve the prosthesis 10, the hooked ribs 12, 13 are advanced and expanded. The arrows in FIG. 7 indicate the direction of advancement of the ribs 12. The desired function of the ribs 12 to expand in this way may be achieved by making the ribs 12 from a superelastic material. The hooked ribs 12, 13 engage their hooks 13 with the permanent wire 14 in one more points as depicted in FIG. 7. Then the ribs 12 are pulled back into the holder 6, which may comprise a tube, thus retracting one or more portions of the permanent wire 14 of the prosthesis 10. As a result, the permanent wire 14 forms a number of loops that reduce in dimension, grouping the distal edge of the prosthesis frame to the convergence region 7, which is dimensionally smaller than the diameter of the external sheath 2, as depicted in FIG. 8. Hence, keeping the tethers 4 fixed in this position, the external sheath 2 is advanced so as to force the prosthesis 10 to collapse into it, as depicted in FIG. 9.

An advantage of a delivery system that has tethers 4 comprising hooked ribs 12, 13 is that it allows retrieval and repositioning of the prosthesis 10 after the implantation procedure has been completed.

The prosthesis delivery system of the present invention may be used in conjunction with any collapsible prosthetic device and is not limited to use with prosthetic heart valves. The average diameter of the prosthesis 10 when in the expanded state is preferably in the range of from 10 to 40 mm, more preferably, the average diameter of the prosthesis 10 is in the range of from 18 to 32 mm. The diameter of the prosthesis when in the compressed state is preferably less than 12 mm. A compressed prosthesis 10 of this size is suitable for transapical access, and more preferably, the diameter of the prosthesis when in the compressed state is less than 8 mm. The axial length of the prosthesis in the expanded state is preferably in the range of from 12 to 200 mm, more preferably from 15 to 55 mm. When in the radially compressed state, the axial length occupied by the prosthesis is increased relative to its expanded state because of the way that the structure folds, however the increase in axial length is less than 100%, preferably less than 80%, and can be as little as 20%.

The invention claimed is:

1. A prosthesis delivery system comprising:
   a sheath defining an axial direction;
   a plurality of tethers movable axially relative to the sheath;
   a holder movable axially within the sheath, wherein the holder is a single tube configured to constrain radially the plurality of tethers; and
   a collapsible prosthesis that is attached to at least one of the plurality of tethers, the collapsible prosthesis comprising a support structure comprising a plurality of apexes, wherein each tether in the plurality of tethers passes through a plurality of the apexes, and further wherein the prosthesis delivery system is configured to deliver the prosthesis to a target position in a living being.

2. The prosthesis delivery system of claim 1, wherein each tether is movable axially within the holder.

3. The prosthesis delivery system of claim 1, wherein a lead end of the holder is configurable to extend beyond a lead end of the sheath.

4. The prosthesis delivery system of claim 1, wherein the holder is movable relative to the sheath between an extended position at which a lead end of the holder extends beyond a lead end of the sheath and a retracted position at which the lead end of the sheath extends beyond the lead end of the holder.

5. The prosthesis delivery system of claim 1, wherein each tether is configured to be controllable to detach the tether from a prosthesis attached to a lead end of the tether via the opposite end of the tether.

6. The prosthesis delivery system of claim 1 wherein the holder is a tube substantially coaxial with the sheath.

7. The prosthesis delivery system of claim 1, wherein each tether comprises an unclosed loop of filiform material.

8. The prosthesis delivery system of claim 1, wherein each tether comprises a hooked rib configured to he movable axially relative to the holder between a collapsed position at which the hooked rib is held by the holder in a deformed state and an expanded position at which the hooked rib extends radially beyond the holder.

9. The prosthesis delivery system of claim 1, wherein, the holder constrains radially the tethers that are configured to attach to a collapsed end of a prosthesis so as to constrain radially the collapsed end of the prosthesis such that the collapsed end of the prosthesis fits within an opening into which the prosthesis is to be withdrawn at a lead end of the sheath.

10. The prosthesis delivery system of claim 1, configured to be inserted into the vasculature of a mammal.

11. The prosthesis delivery system of claim 1, wherein the plurality of tethers comprises three tethers.

12. The prosthesis delivery system of claim 1, wherein the plurality of tethers comprises four tethers.

13. The prosthesis delivery system of claim 1, wherein the target position is an organ of a living being.

14. The prosthesis delivery system of claim 13, wherein the organ is a heart.

15. The prosthesis delivery system of claim 1 sized to deliver the prosthesis through the vasculature of the living being.

16. The prosthesis delivery system of claim 1, wherein the support structure is collapsible from a fully expanded state into a compressed state by pulling on the apexes and can be drawn into the sheath when it is in the compressed state.

17. A method of collapsing a prosthesis to a collapsed state in a sheath using the prosthesis delivery system of claim 1, the method comprising the steps of:
   constraining radially with the holder the plurality of tethers, each of which is attached to the prosthesis; and
   moving the tethers and the holder axially within the sheath such that the prosthesis is forced to collapse into the sheath and the holder is retracted into the sheath.

18. The method of claim 17, further comprising the step of:
   moving the tethers axially through the holder so as to bring a lead end of each tether attached to the prosthesis towards the holder so as to collapse partially the prosthesis.

19. A method of delivering a prosthesis collapsed in a sheath to a target position using the prosthesis delivery system of claim 1, the method comprising the steps of:
   retracting the sheath axially away from the prosthesis attached to the plurality of tethers such that the prosthesis partially expands from the collapsed state, wherein the tethers to which the prosthesis is attached are constrained radially by the holder that is movable axially within the sheath;
   positioning in the target position the prosthesis that is in as partially collapsed state, attached to the tethers; and
   relaxing the tension in the tethers.

* * * * *